United States Patent [19]

Conrad

[11] Patent Number: 4,704,910

[45] Date of Patent: Nov. 10, 1987

[54] METHOD AND APPARATUS FOR AUTOMATIC SAMPLING OF GASES

[75] Inventor: Rodney W. Conrad, Denver, Colo.

[73] Assignee: Romed Corporation, Denver, Colo.

[21] Appl. No.: 667,767

[22] Filed: Nov. 2, 1984

[51] Int. Cl.⁴ .............................................. G01N 1/24
[52] U.S. Cl. ............................... 73/863.21; 73/863.31; 422/88; 422/101
[58] Field of Search ........... 73/863.21, 863.31, 863.33; 422/88, 101

[56] References Cited

U.S. PATENT DOCUMENTS

| | | |
|---|---|---|
| 3,043,145 | 7/1962 | Hoffman . |
| 3,362,222 | 1/1968 | Johnson et al. ........................ 73/198 |
| 3,369,405 | 2/1968 | Galegar . |
| 3,731,539 | 5/1973 | Brittan .............................. 73/863.31 |
| 3,884,081 | 5/1975 | Griffith . |
| 4,090,392 | 5/1978 | Smith et al. . |
| 4,454,772 | 6/1984 | Brunner ............................ 73/863.31 |

Primary Examiner—Michael J. Tokar
Assistant Examiner—Tom Noland
Attorney, Agent, or Firm—John E. Reilly

[57] ABSTRACT

A method and apparatus for continuously monitoring gases exhaled by animals in a laboratory environment for the presence of hepatic bilirubin permits long-term monitoring in which samples are directed into each of a series of sample containers by evacuating each container over a selected time interval while retaining the other containers in a closed position. The gas supply and gas evacuation lines to and from each sample container are simultaneously controlled via a programmer controlled circuit to permit automated sequential filling of the sample containers over a long-term interval. The sample containers are mounted in a wall-mounted cabinet having hinged display shelves for the containers with a common control panel behind the shelves to regulate the sampling and filling operation.

12 Claims, 7 Drawing Figures

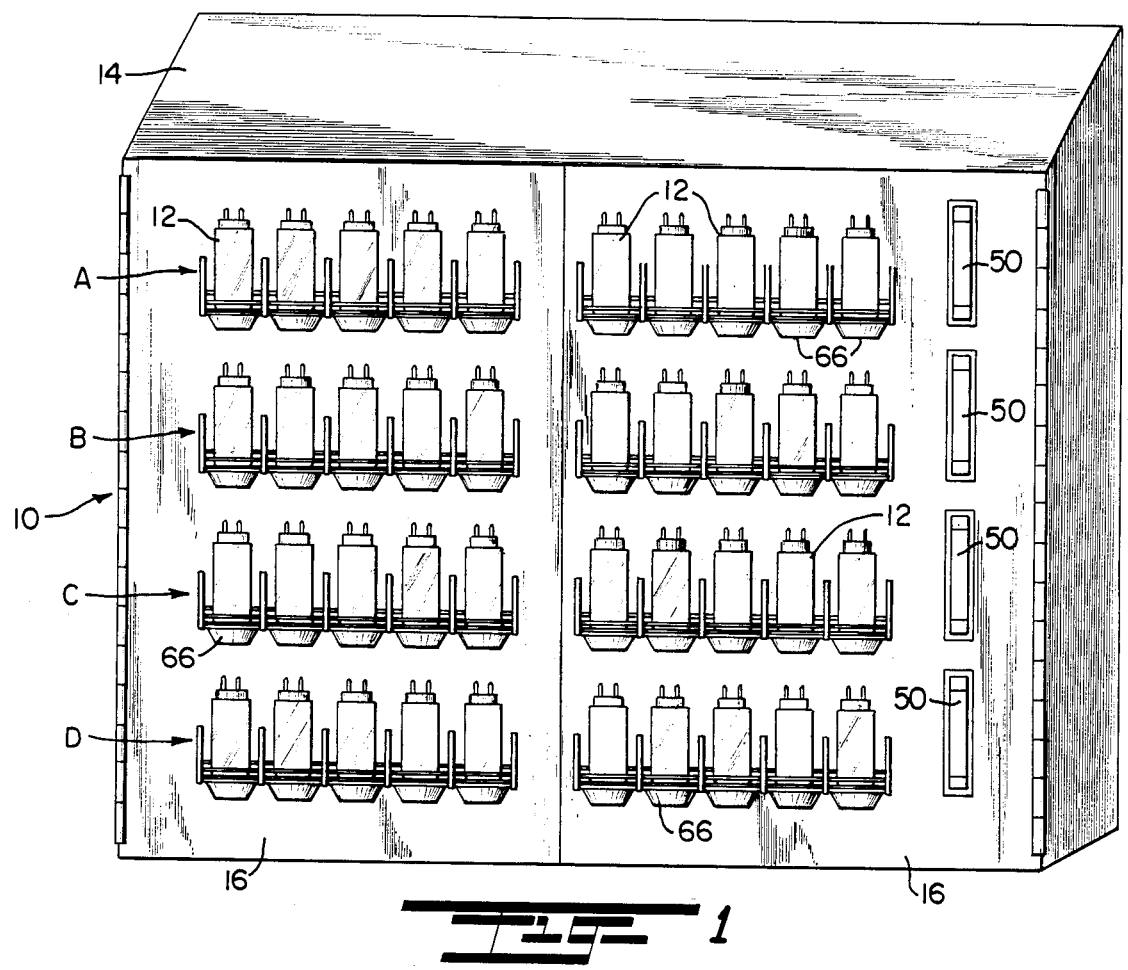
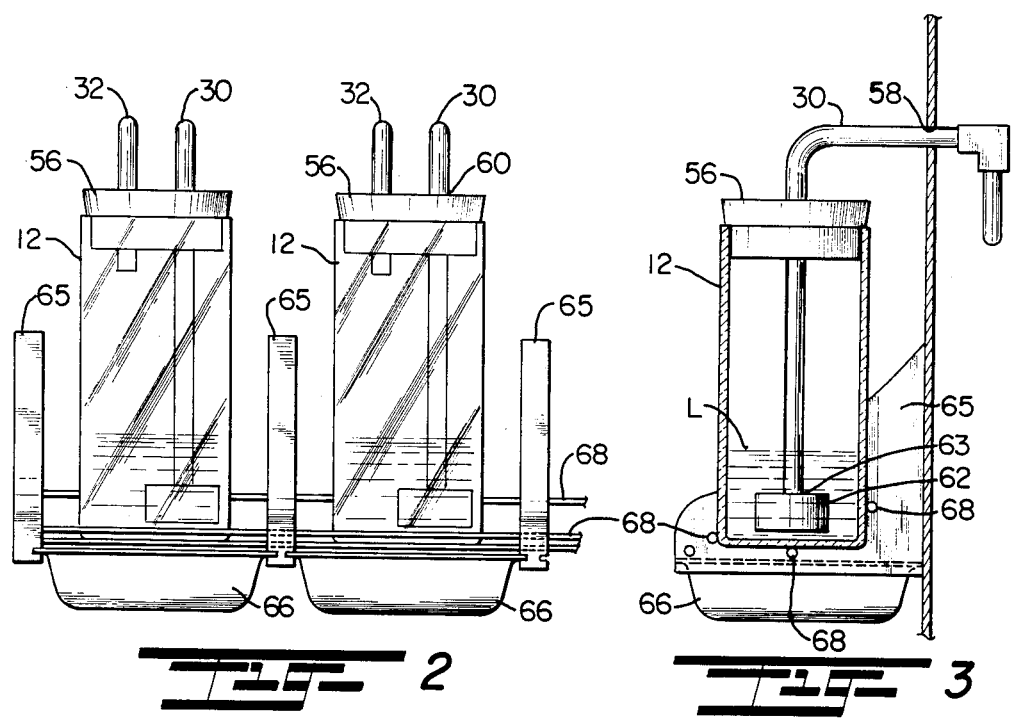

METHOD AND APPARATUS FOR AUTOMATIC SAMPLING OF GASES

Specification

This invention relates generally to the field of gas analysis for use in medical laboratory procedures; and more particularly is directed to an automatic system which is capable of sampling gases from a plurality of sources and directing the samples into a series of bottles sequentially at predetermined timed intervals for washing and subsequent analysis.

BACKGROUND AND FIELD OF THE INVENTION

It is a standard laboratory procedure to measure and analyze the gases exhaled by laboratory animals, such as, rats to determine the presence of disease in the blood. Customarily, this has been accomplished by a gas washing procedure which involves directing the flow of exhaled gases through a liquid in order to capture some property present in the exhaled product. For example, measurement of the carbon monoxide level provides an indication of hepatic bilirubin production in the animal. The gas washing procedure entails the steps of drawing exhaled air from the cage, converting the carbon monoxide present in the air to carbon dioxide, then bubbling or washing the carbon dioxide through a bottle filled with a liquid, typically ethanolamine, for a predetermined time interval followed by measuring the amount of carbon monoxide recovered in the liquid. In the past this has required the tedious procedure of manually directing the gas into a succession of bottles over an extended time period. Continuous effort and supervision by an operator is required in order to obtain samples at timed intervals over periods as long as twenty-four hours. After each bottle is filled, it must be sealed and removed to an analysis chamber to evaluate the gases therein.

More recently, the procedure of collecting fluid samples for various purposes, not necessarily involving gas washing, has been facilitated by the use of automated apparatus for collecting one or a plurality of gas samples into bottles for analysis. For example, U.S. Pat. No. 3,362,222 to W. K. Johnson et al teaches the use of a plurality of evacuated bottles connected to a fluid stream by normally closed tubes; solenoid-actuated valves are automatically and sequentially opened at timed intervals to allow fluid to flow through the tubes and into the bottle. The apparatus described in U.S. Pat. No. 3,043,145 to H. T. Hoffman also utilizes solenoid valves to control sampling of fluid: the fluid to be analyzed is drawn from different sources through sample lines into a manifold by a washer pump, and after washing, the pump delivers the sample to a gas analyzer. U.S. Pat. Nos. 4,090,392 to I. I. Smith et al and 3,369,405 to R. R. Galegar are directed to computer controlled systems for sampling fluid from different locations, utilizing solenoid valves to sequentially or simultaneously open a number of sample lines. Despite advantages such systems might make in a gas washing application, there remains a need for an apparatus which is capable of improving the efficiency and accuracy of the gas washing procedure by providing a compact system for collecting gas samples over extended time periods and which requires little or no observation or active participation by the laboratory technician.

SUMMARY OF THE INVENTION

It is therefore an object of the present invention to provide for a novel and improved compact apparatus which increases the efficiency of gas washing and similar procedures by providing computer controlled means for automatically collecting gas samples from one or more sources, then directing each sample successively at predetermined intervals to one of a series of bottles, followed by washing or bubbling the gas for a preselected length of time into each bottle.

It is another object of the present invention to provide a gas washing apparatus which can be housed entirely within a cabinet or similar compact housing for improved space efficiency and convenient use, and which can be constructed from durable relatively low cost materials.

A further object of the present invention is to provide for a novel and improved gas washing apparatus for monitoring of gases from a plurality of sources, including automatic valving means controlling the sequential intake of gas samples into each of a series of bottles, means for controlling the length of time and rate of flow at which the samples are washed into each bottle as well as means for automatically sealing the bottle after completion of the washing for subsequent analysis.

It is an additional object of the present invention to provide for computer controlled apparatus which is capable of performing a gas washing procedure on a series of gas samples taken at predetermined timed intervals from a plurality of sources, and which requires a minimum of supervision on the part of the operator.

It is a still further object of the present invention to provide for an automated gas washing method and apparatus which is particularly adapted to simplify and improve the efficiency of measuring hepatic bilirubin production in laboratory rats, and which is capable of generating a large quantity of data over long-term intervals without supervision.

An additional object of the present invention is to provide a gas washing apparatus wherein the sample lines to a series of sample bottles are enclosed in a protective housing, yet are easily accessible for adjustment or observation, while the sample bottles are displayed clearly on the exterior of the housing for visual observation and accessibility for installation and removal; and further wherein one or more filled sample bottles can be removed without interrupting the filling process to other bottles.

In accordance with the present invention, a gas-washing apparatus has been devised for sequential sampling of gas over a predetermined time interval and is particularly adaptable for use in measuring and analyzing gases exhaled by laboratory animals in a controlled environment to determine the presence of disease in the blood, such as, hepatic bilirubin production in rats. To this end, the gas washing apparatus of the present invention comprises a plurality of sample containers, a vacuum source including a gas evacuation line from the source to each of the sample containers, and a gas delivery or supply line extending from the source of gas to each of the sample containers. Means are provided for connecting the gas supply and gas evacuation lines to each of the sample containers including valve control means which normally close the gas supply and gas evacuation lines to each sample container. Activating means associated with the valve control means is operative to simultaneously open the gas supply and gas evacuation lines to each sample container in succession whereby to evacuate each container in order to draw gas from the gas supply line into the sample container, the activating means being responsive to an electrical signal to retain the valve control means for each sample container in the open position over a predetermined time interval. Timer means transmit electrical signals to the activating means at predetermined time intervals to sequentially open the valve control means for each sample container in succession while the valve control means for the other sample containers are retained in a closed position. In a preferred embodiment of the present invention, the sample containers are in the form of bottles which are arranged in rows on a display shelf which is hinged to a wall cabinet with the necessary supply and evacuation lines as well as electrical control panels conveniently mounted behind the display shelf or shelves.

In the method of the present invention for continuously monitoring gases for the presence of hepatic bilirubin production in rats in a laboratory environment, the gases exhaled by the rats are directed from each cage into a main collection chamber in which carbon monoxide is converted to carbon dioxide and thereafter the resultant gas is delivered via a gas supply line to each of a series of sample containers, each container being partially filled with a liquid, and the gas supply line and gas evacuation line being secured in airtight relation to each sample container. In a predetermined sequence, a quantity of the gases is delivered into each sample container by evacuating the container over a selected time interval while retaining the gas supply lines to the other containers in a closed position, and followed by closing the supply to each sample container once filled so that the sample container may be removed.

The above and other objects, advantages and features of the present invention will become more readily understood and appreciated from a consideration of the following detailed description of a preferred embodiment of the present invention when taken together with the accompanying drawings in which:

BRIEF DESCRIPTION OF THE DRAWINGS

FIG. 1 is a perspective view of the gas washing apparatus of the present invention, illustrating the arrangement of the sample bottles on the exterior of the apparatus housing;

FIG. 2 is an enlarged front view in detail of the sample bottles of FIG. 1;

FIG. 3 is a side view in section of a sample bottle and shelf of the apparatus;

DETAILED DESCRIPTION OF THE PREFERRED EMBODIMENT

Figure 4:
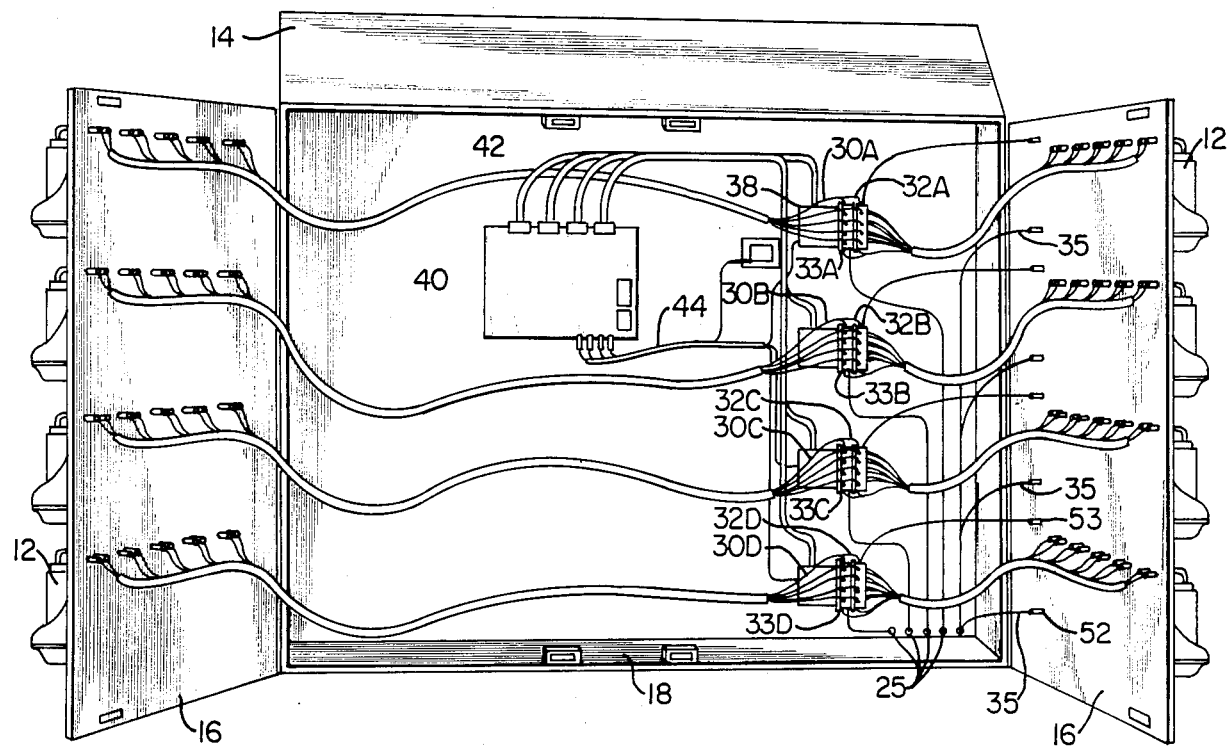
FIG. 4 is a front view in elevation of the gas washing apparatus illustrated with the door of the housing in the open position.

Referring to FIGS. 1 to 4, the gas washing apparatus 10 includes a plurality of sample bottles 12 arranged across the front of a housing 14. The housing comprises a cabinet provided with a pair of doors or shelves 16 opening outwardly from the center of the cabinet in opposite directions. For purposes of illustration, the bottles 12 are arranged in horizontal rows A, B, C and D across the door 16, and each series of bottles 12 in a given row receives gas samples from a different source, such as, from different rat cages (not shown). Therefore, as illustrated in FIG. 1, the apparatus 10 can accommodate a sampling system of ten bottles for gases collected from each of four cages, so as to permit four tests to be run in succession.

Figure 5:
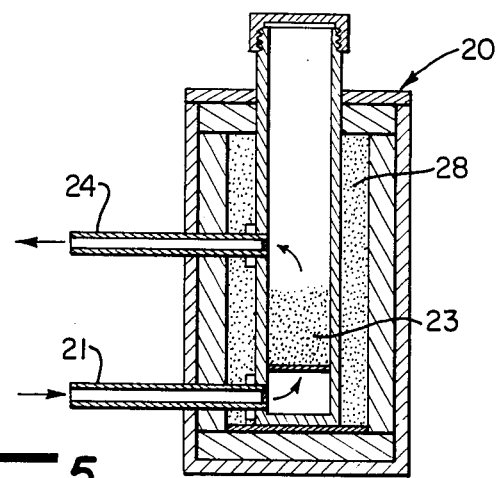
FIG. 5 is a vertical cross-sectional view of a Hopcalite chamber used in treatments of the gases to be analyzed prior to washing.

In FIG. 4, the cabinet 14 is shown with its shelves 16 in the open position to illustrate the means for automatically delivering gas samples from different sources to each row or series A, B, C, D of sample bottles 12 for washing and subsequent analysis. More particularly, a Hopcalite chamber 20 illustrated in FIG. 5 receives gas from each of the four cages through inlet ports 21 and in a well-known manner oxidizes the expired carbon monoxide in the gas into carbon dioxide by passing it through a column of Hopcalite 23. The oxidized gas is delivered through outlet port 24 to main supply lines 25 shown in FIG. 4. The Hopcalite chamber 20 may be of conventional construction and is provided with a temperature regulator and suitable insulation 28 to maintain the column of Hopcalite 23 at a constant temperature.

Figure 6:
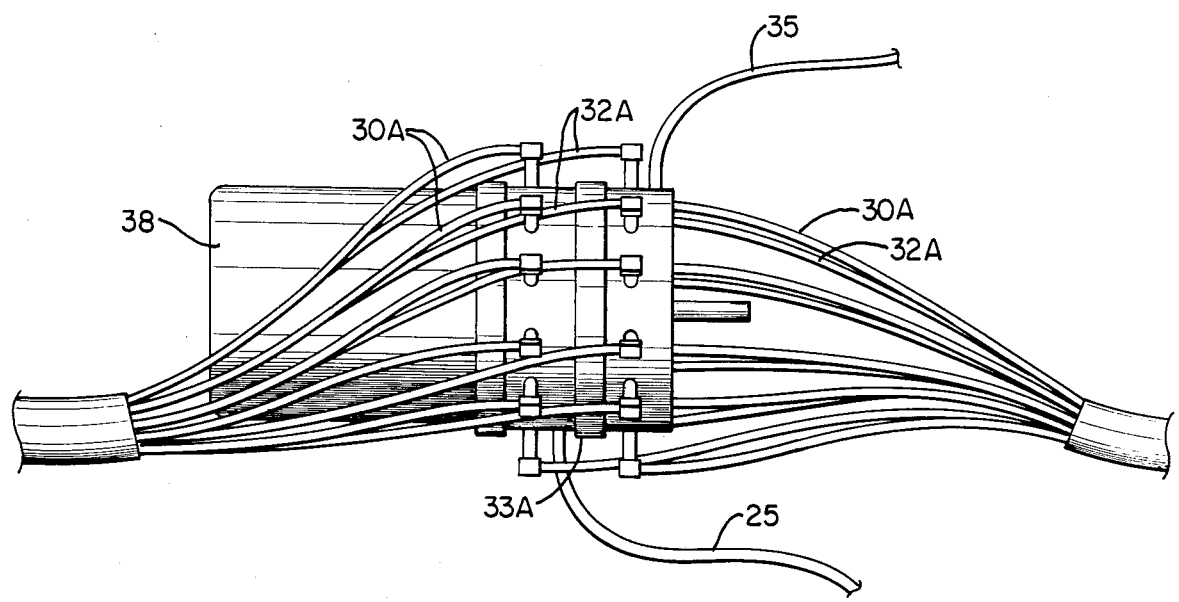
FIG. 6 is an enlarged view of the preferred form of rotary valve employed in accordance with the present invention.

As best seen from FIGS. 4 and 6, the main supply lines 25, each carrying gas delivered from a single cage, enter the cabinet 14 through the bottom panel 18 thereof and each line communicates with a plurality of branch gas lines 30A, 30B, 30C and 30D leading to a corresponding row A, B, C, D of bottles. Solenoid-controlled rotary valves 33A, 33B, 33C and 33D are provided with wafers which selectively open and close each of the branch gas lines 30A to 30D at timed intervals in order to control the flow of gas to each bottle 12 in the rows, as will be described hereinafter in greater detail. Similarly vacuum lines 35 from an external vacuum pump, not shown, enter the cabinet adjacent the main gas supply lines 25 and each vacuum line 35 is connected via a flow meter 50 to a rotary valve 33 in a manner later described. At the rotary valve 33, the main vacuum lines 35 communicate with a plurality of auxiliary vacuum lines 32A, 32B, 32C, 32D which in turn communicate with each bottle 12 in corresponding rows A, B, C and D. The vacuum pump, through the main and auxiliary vacuum lines 35, 32, creates negative pressure in the bottles 12 to cause gas from the branch gas line 30 to be drawn into bottles 12. As previously described with reference to the branch gas lines 30, each auxiliary vacuum line 32 for a row of bottles A, B, C, D is controlled by the solenoid valve 33 associated with that row. When the rotary valve 33 receives a signal from a printed circuit board 40 to supply gas to the bottles 12 in the corresponding row, the plungers of the valve 33 will retract to simultaneously open the branch gas line 30 and auxiliary vacuum line 32 associated with that bottle. The negative pressure in the vacuum line 32 thus opened will create a vacuum within the bottle 12 which causes gas flowing through the branch gas line 30 to be drawn into the bottle 12 for washing. The printed circuit board 40 is provided which automatically controls the solenoids 38 of rotary valve 33 through upper control lines 42 in accordance with commands programmed into an external computer, not shown, but which may be a Northstar Horizon Computer, manufactured and sold by Northstar of Minneapolis, Minn. More particularly, each rotary valve 33 contains a switching chamber which, when a pulse is received from the printed circuit board 40 through the upper control lines 42, will simultaneously open two valves for the bottle 12 which is to receive gas at that time: one valve to open the vacuum line 32, and the other valve to open the branch gas supply line 30 to the bottle. Lower feedback lines 44 extend from each solenoid 38 back to the printed circuit board 40 to transmit a signal informing the computer which valves have been opened to a bottle 12, and in which row A, B, C or D.

Referring to FIG. 1, indication of the rate of flow of the gas into the sample bottle 12 can be visually observed by means of the flow meters 50 which are mounted on the exterior of the cabinet door 16 adjacent each row A, B, C, D of bottles 12. As illustrated in FIGS. 4 and 6, the main vacuum line for each row is directed to a corresponding port on the inner wall of the cabinet door 16. Each vacuum line 35 opens into one of the flow meters 50 through lower port 52 and exit through upper port 53. The vacuum line is then connected through the rotary valve 33 to auxiliary vacuum line 32 as described above. The provision of flow meters allows the operator to monitor the level of negative pressure produced in the main vacuum line and thus to regulate the rate of flow of the gas into the bottles 12 in each row when the valves are open.

The sample bottles 12 are shown in greater detail in FIGS. 2 and 3. The bottles themselves may be of any appropriate size and shape, and standard bottles for laboratory use are particularly adaptable for use with the gas washing apparatus. The bottles are provided with tight-fitting rubber stoppers 56 which provide an airtight seal. The gas branch supply line 30 projects through an aperture 58 in the cabinet door 16 and extends into the bottle 12 through an aperture 60 in the rubber stopper 56. The bottle is partially filled with a liquid L which is used in washing the gas, such as, ethanolamine. The gas line 30 extends into the liquid L, and the open end 63 of the line 30 is provided with a diffuser 62. The gas flowing through the line 30 is released or bubbled through the diffuser 62 into the liquid L for washing. The flow of gas into the liquid continues for a predetermined period of time to complete the washing procedure for that particular sample. After the requisite time interval, the solenoids 38 are activated in a manner hereinafter described to switch the chamber in the valve 33 associated with the first set of vacuum and gas lines 32, 30 in each row so that wafers in those lines close and the plungers in the vacuum and gas lines 32, 30 leading to the next bottle in the row are opened to cause a gas sample to flow into that bottle for washing. The selective opening and closing of the valve continues at timed intervals for successive bottles 12 in each row to permit gas samples to be washed in each of the bottles in the row. At the same time, gas samples from different sources are released into corresponding bottles in each of the remaining rows. When samples have been washed in the desired number of bottles in each row, a signal is directed via the printed circuit board 40 to instruct the computer not to transmit another signal. Any or all of the bottles 12 can be removed from the cabinet 14 for analysis and comparison without interrupting the process. For example, since switching or advancing of the rotary valve 33 simultaneously controls both the vacuum and the gas supply lines 32, 30 for each bottle, when the washing operation has been completed for any bottle and the valve 33 has been rotated to open the lines to the next bottle, the first bottle receiving the sample can be individually removed for analysis without interrupting the process.

The bottles are retained on the outer surface of the door 16 by a relatively simple shelving arrangement. As shown in FIGS. 2 and 3, sidewalls 65 project at substantially right angles away from the outer surface of the doors 16, and adjacent pairs of sidewalls 65 are connected by a lower drip tray 66 which may be a conventional laboratory weigh boat. As will be noted, the sidewalls 65 are shared by adjacent bottles 12 in order to promote efficiency of space by providing a continuous shelving unit the substantial width of the door. However, each bottle support could be provided with separate sidewalls 65 if so desired. The bottles 12 are supported above the weigh boats or trays 66 by horizontal support bars 68 which extend between the sidewalls and are arranged to engage the front, rear and bottom surfaces of the bottle to hold it above the tray and prevent tipping or shifting. The support bars 68 preferably extend continuously through apertures in all of the sidewalls 65 in a given row on a door 16 of the housing, as shown in FIG. 2; or, if desired, each bottle support may be provided with separate support bars 68.

The preferred embodiment illustrated in the drawings is set up to accommodate samples flowing from four cages into each of the four rows, so that at the end of the procedure each of the rows represents ten samplings of the gas taken from a single cage over a period of time, for example, one hour per bottle. The apparatus could of course be modified to collect the gas from eight cages, each cage supplying samples into five bottles in each row. A separate valve would be provided to tie in the main gas supply lines 25 from two cages into a single row; and, by switching the valve between the supply lines 25 from each of the cages, gas from one cage could be directed into the first five bottles in the row, while gas from the second cage would be supplied into the second group of five bottles in the row. If the conditions of the laboratory or of the particular test being conducted require that samples be collected from fewer than four different cages, then it is necessary only to program the apparatus for sample collection in a corresponding number of rows.

Figure 7:
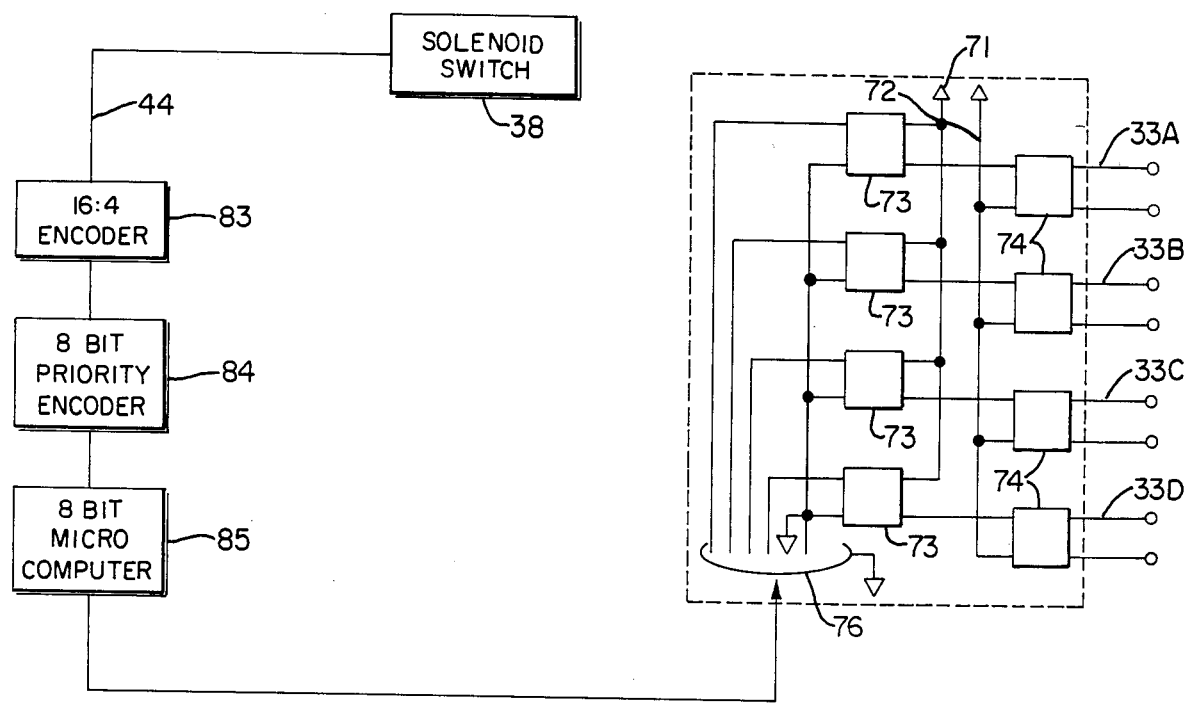
FIG. 7 is a flow diagram illustrating a typical form of computerized control circuit for the gas washing apparatus of the present invention.

In the preferred embodiment as described, each rotary valve 33 is a fluid switch wafer Model No. W60 manufactured and sold by Scanivalve Corporation of San Diego, Calif. Each solenoid 38 is a Model No. WS5-12-95VDC and the plunger associated with each solenoid 38 is a Model No. W1260-1P-12T, also manufactured and sold by Scanivalve Corporation. In the control circuit illustrated in FIG. 7, a main or high power source, not shown, is connected directly into a series of solid state relays 73 and bridge rectifiers 74 via output lines 71 and 72. A solid state relay 73 and bridge rectifier 74 are provided for each of the valves 33A to 33D, inclusive, each relay 73 receiving pulses from a computer port as represented at 76 to activate the solenoid for its associated rotary valve 33 a number of times corresponding to the number of positions on the rotary valve switch chamber. For example, for a series of ten bottles for each rotary valve, ten separate solenoid controls on the rotary valve serve to simultaneously activate each pair of backing and supply lines to a bottle. The bridge rectifiers 74 serve to convert the alternating current power source into direct current for activation of each valve 33. The power source is also directed into a step-down transformer circuit, not shown, the latter transforming the high voltage power source to a low voltage source on the order of 5 volts into feedback lines 44 from the solenoids 38 and which are connected respectively to encoders 83 and 84. Encoder 83 may be any suitable form of four-digit encoder for each valve 33, such as, a No. 4532 8:3 encoder. Each encoder 84 may suitably be a 4532 10:4 encoder and is connected via microcomputer 85 to each port 76.

From the foregoing, the printed circuit board 40 receives commands from the computer and delivers same via upper control lines 42 for the purpose of controlling each rotary valve 33. Again, when a pulse is received from the computer through one of the control lines 42, it is operative to simultaneously open a vacuum and supply line for each bottle for the purpose of filling the bottle over a predetermined time interval. Lower feedback lines 44 extend from each solenoid control for a valve back to a printed circuit board 40 to transmit signals informing the computer which valve has been opened and in which row. Once a sample has been delivered into the last bottle to be washed in each row, a feedback signal is directed to the computer to terminate the gas washing operation and specifically to instruct the computer not to transmit any more pulses.

In a typical operation, the washing and filling of each bottle may run for periods on the order of one hour each in order to obtain an accurate sampling over an extended time span on the order of ten hours. The cabinet design facilitates ease or removal and installation of the bottles and as mentioned the rotary valve control permits individual removal of each bottle for separate analysis when desired. With the system of the present invention, as many as four different sampling processes may be conducted either simultaneously or in direct succession. If desired, the sampling period for the bottles in each row may be varied independently of the other rows as well as the number of bottles to be filled in each row. Accordingly, the system is extremely versatile, compact and lends itself well to automatic regulation and accurate control.

It is therefore to be understood that various modifications and changes may be made in the precise construction and arrangement of elements comprising the preferred form of the present invention without departing from the spirit and scope thereof as defined by the appended claims.

I claim:

1. Gas washing apparatus for sequentially selecting samples of gas from a common source of gas over a predetermined time interval comprising:

a plurality of sample containers, an outer housing including at least one display shelf, and support means operative to support said sample containers in a row on said display shelf;

a vacuum source including a gas evacuation line from said vacuum source to each of said sample containers, and a gas supply line extending from said source of gas to each of said sample containers;

menas for connecting said gas supply lines and gas evacuation lines to each of said sample containers;

valve control means normally closing said gas supply and gas evacuation lines to each said sample container including activating means associated with said valve control means and operative to simultaneously open said gas supply line and gas evacuation line to each said sample container in succession whereby to evacuate each said sample container in succession in order to draw gas via said open gas supply line into said sample container from said source of gas, said activating means responsive to a control signal to retain said valve control means for each said sample container in the open position over a predetermined time interval;

control circuit means for transmitting said control signals sequentially ot said activating means at predetermined timed intervals whereby to sequentially open said valve control means for each said sample container while said valve control means for all other said sample containers are in a closed position; and a control panel associated with said housing, said valve control means on said control panel, and said gas evacuation and gas supply lines extending from said source of gas through said display shelf for connection to said containers.

2. Apparatus according to claim 1, there being a plurality of display shelves in vertically spaced relation to one another, said containers being arranged in rows, each row of containers having gas supply lines connected to a different source of gas, and common valve control means for each said row of containers.

3. Apparatus according to claim 2, said supporting means for said containers defined by drip trays extending horizontally at vertically spaced intervals across said display shelf, each said row of said containers disposed in juxtaposed relation to one another in each drip tray, each said drip tray including horizontal support bars upon which said containers are mounted.

4. Apparatus according to claim 1, including means for mounting said display shelf in hinged relation to said housing.

5. Apparatus according to claim 1, said gas supply lines including a main gas supply line extending from said source of gas to said valve control means, and auxiliary gas supply lines extending from said valve control means to each of said sample containers.

6. In the method for continuous monitoring of gases, particularly carbon monoxide, for the presence of hepatic bilirubin production in rats wherein the rats are collected in cages and gases exhaled by the rats are directed from each cage into a main collection chamber wherein carbon monoxide present is converted to carbon dioxide and thereafter the resultant gas is delivered to a manifold provided with a valve control for each of a series of sample containers, there being a gas supply line extending from said manifold to each of said sample containers and a gas evacuation line extending from a source of vacuum to each of said sample containers, the steps comprising:

(a) partially filling each said sample container with a liquid and mounting the gas supply line and gas evacuation line in airtight relation to each container;

(b) simultaneously opening said gas supply line and gas evacuation line to each container for a predetermined time interval while closing said gas supply lines and gas evacuation lines to all of said other containers;

(c) sensing the rate of flow of gas to each said sample container and correlating the rate of flow with the time interval necessary to fill each said sample container;

(d) sequentially activating said valve control after a predetermined time interval to successively open said gas supply line and gas evacuation line to each successive sample container while closing the gas supply line and gas evacuation lines to all of the other containers; and (e) followed by disconnecting each said sample container from its associated gas supply and gas evacuation lines while retaining each sample collected in a sealed condition within each respective container for subsequent analysis and testing.

7. Gas washing apparatus for sequentially selecting samples of gas from a common source of gas over a predetermined time interval comprising:

a plurality of sample containers;

a vacuum source including a main gas evacuation line from said vacuum source and a main gas supply line extending from said source of gas;

means for connecting said main gas supply line and main gas evacuation line to each of said sample containers including valve control means normally closing said main gas supply and main gas evacuation lines to each said sample container, an auxiliary gas supply line and an auxiliary gas evacuation line extending between said valve control means and each said sample container, and activating means associated with said valve control means and operative to simultaneously establish communication between said main gas supply line and main gas evacuation line with a respective auxiliary gas supply line and gas evacuation line to each said sample container in succession whereby to evacuate each said sample container in succession in order to draw gas into said sample container from said source of gas, said activating means being responsive to an electrical signal to retain said valve control means for each said sample container in the open position over a predetermined time interval;

an outer wall-mounted housing, a display shelf for each said row of containers on said housing, a control panel in said housing behind said display shelves, said valve control means mounted on said control panel and said auxiliary gas evacuation and gas supply lines extending from said source of gas and vacuum source through said display shelves for connection to said containers; and control circuit means for transmitting electrical signals sequentially to said activating means at predetermined timed intervals whereby to sequentially open said valve control means to draw gas into each said sample container while said valve control means remains in a closed position to said other sample containers.

8. Apparatus according to claim 7, including means for mounting said display shelves in hinged relation to said housing, drip trays extending horizontally at vertically spaced intervals across said display shelves, each said row of said containers disposed in juxtaposed relation to one another in each said drip tray.

9. Apparatus according to claim 8, each said drip tray including horizontal support bars upon which said containers are mounted.

10. Apparatus according to claim 7 wherein said containers are arranged in rows and further including a flow meter associated with each row of said containers, each said auxiliary gas supply line extending via one of said flow meters to said valve control means.

11. In the method for continuous monitoring of gases, particularly carbon monoxide, for the presence of hepatic bilirubin production in rats wherein the rats are collected in cages and gases exhaled by the rats are directed from each cage into a main collection chamber wherein carbon monoxide present is converted to carbon dioxide and thereafter the resultant gas is delivered to a valve, there being a gas supply line extending from said valve to each of a series of sample containers and a gas evacuation line extending from a source of vacuum to each of said sample containers, the steps comprising:

(a) partially filling each said sample container with a liquid and mounting the gas supply line and gas evacuation line in airtight relation to each container;

(b) simultaneously opening said gas supply line and gas evacuation line to each container for a predetermined time interval while closing said gas supply lines and gas evacuation lines to all of said other containers;

(c) sequentially advancing said valve after a predetermined time interval to successively open said gas supply line and gas evacuation line to each successive sample container while closing the gas supply line and gas evacuation lines to the other containers; and (d) followed by disconnecting each said sample container from its associated gas supply and gas evacuation lines while retaining each sample collected within each respective container for subsequent analysis and testing.

12. Apparatus according to claim 11, including the step of sensing the rate of flow of gas to each said sample container and correlating the rate of flow with the time interval necessary to fill each said sample container.

* * * * *